(12) United States Patent
Liang et al.

(10) Patent No.: US 11,346,910 B2
(45) Date of Patent: May 31, 2022

(54) MRI DISPLAY OUTPUT REFLECTING CONTRAST AGENT CONCENTRATION AS A FUNCTION OF TIME

(71) Applicant: Hologic, Inc., Marlborough, MA (US)

(72) Inventors: Jiachao Liang, Palo Alto, CA (US); Jimmy R. Roehrig, Aptos, CA (US)

(73) Assignee: Hologic, Inc., Marlborough, MA (US)

( * ) Notice: Subject to any disclaimer, the term of this patent is extended or adjusted under 35 U.S.C. 154(b) by 454 days.

(21) Appl. No.: 16/534,545

(22) Filed: Aug. 7, 2019

(65) Prior Publication Data
US 2019/0361081 A1 Nov. 28, 2019

Related U.S. Application Data

(63) Continuation of application No. 14/384,636, filed as application No. PCT/US2013/032681 on Mar. 15, 2013, now abandoned.

(60) Provisional application No. 61/611,877, filed on Mar. 16, 2012.

(51) Int. Cl.
| G01R 33/56 | (2006.01) |
| A61B 5/00 | (2006.01) |
| G01R 33/50 | (2006.01) |
| A61B 5/055 | (2006.01) |

(52) U.S. Cl.
CPC .......... *G01R 33/5601* (2013.01); *A61B 5/055* (2013.01); *A61B 5/742* (2013.01); *G01R 33/50* (2013.01)

(58) Field of Classification Search
CPC ........ A61B 5/055; A61B 5/742; G01R 33/50; G01R 33/5601
See application file for complete search history.

(56) References Cited

U.S. PATENT DOCUMENTS

| 7,693,320 B2 | 4/2010 | Degani et al. |
| 7,949,164 B2 | 5/2011 | Degani et al. |
| 8,175,366 B2 | 5/2012 | Degani et al. |
| 2008/0125643 A1 | 5/2008 | Huisman et al. |

OTHER PUBLICATIONS

Jansen, Shimauchi, Zak, Fan, Wood, Karczmar, Newstead. AJR2009; 193:832-839, Kinetic Curves of Malignant Lesions are Not Consistent Across MRI Systems: Need for Improved Standardization of Breast Dynamic Contrast-Enhanced MRI Acquisition (8 pages).

CK Kuhl, PM Mielcareck, S Klaschnik, C Leutner, E Wardelmann, J Gieseke, H Schild, Radiology. 1999 211:101-110. Dynamic Breast MR Imaging: Are Signal Intensity Time Course Data Useful for Differential Diagnosis of Enhancing Lesions? (10 pages).

Haacke EM, Tkach JA. Fast MR imaging: techniques and clinical applications. AJR Am J Roentgenol. 1990; 155(5):951-64. (14 pages).

(Continued)

*Primary Examiner* — Michael T Rozanski
(74) *Attorney, Agent, or Firm* — Merchant & Gould P.C.

(57) ABSTRACT

A magnetic resonant imaging (MRI) review workstation includes a control processor, and a display integrated or otherwise operatively coupled with the control processor, wherein the control processor is configured to receive and analyze magnetic resonant imaging information pertaining to an imaged volume of tissue, and to cause to be displayed on the display output information that reflects or is otherwise indicative of an absorption rate of a contrast agent in the volume of tissue.

18 Claims, 9 Drawing Sheets

(56) References Cited

OTHER PUBLICATIONS

Frahm J, Haase A, Matthaei D. Rapid three-dimensional MR imaging using the FLASH technique. J Comput Assist Tomogr. 1986; 10(2):363-8. (6 pages).
Tofts PS, Kermode AG. Measurement of the blood-brain barrier permeability and leakage space using dynamic MR imaging. 1. Fundamental concepts. MRM 1991; 17(2):357-67. (11 pages).
Brix G, Semmler W, Port R, Schad LR, Layer G, Lorenz WJ. Pharmacokinetic parameters in CNS Gd-DTPA enhanced MR imaging. J Comput Assist Tomogr. 1991; 15(4):621-8. (26 pages).
Rohrer M, Bauer H, Mintorovitch J, Requardt M, Weinmann HJ. Comparison of Magnetic Properties of MRI Contrast Media Solutions at Different Magnetic Field Strengths. Invest Radiol. 2005; 40(11):715-24. (10 pages).
C Kuhl, Radiology. 2007 244:356-378. The Current Status of Breast MR Imaging (23 pages).
Brix G, Kiessling F, Lucht R, Darai S, Wasser K, Delorme S, Griebel J. Microcirculation and Microvasculature in Breast Tumors: Pharmacokinetic Analysis of Dynamic MR Image Series. Magn Reson Med. 2004; 52(2):420-9. (10 pages).
Stanisz GJ, Odrobina EE, Pun J, Escaravage M, Graham SJ, Bronskill MJ, Henkelman RM. T1, T2 relaxation and magnetization transfer in tissue at 3T. Magn Reson Med. 2005; 54(3):507-12. (6 pages).
PCT International Search Report and Written Opinion for PCT/US13/32681, dated Jun. 17, 2013, Applicant Hologic, Inc., forms PCT/ISA/210, 220 and 237 (12 pages).
Hoffman et al. "Pharmacokinetic Mapping of the Breast: A New Method for Dynamic MR Mammography" Magnetic Resonance in Medicine 33: 506-514 (1995).

| Characteristic | System 1 | System 2 | System 3 |
|---|---|---|---|
| Dates used | May 2002 - September 2005 | September 2005 - April 2007 | September 2005 - April 2007 |
| Unit | 1.5-T Genesis Signa (GE Healthcare) | 1.5-T Signa Excite (GE Healthcare) | 1.5-T Achieva (Philips Healthcare) |
| No. of coil channels | 4 | 8 | 7 |
| Acquisition plane | Coronal | Axial | Axial |
| Pulse sequence | 3D spoiled gradient-recalled echo | 3D fast gradient-recalled echo | 3D fast-field echo |
| TR/TE | 7.7/4.2 | 4.3/2.0 | 7.9/3.9 |
| Flip angle | 30° | 10° | 10° |
| Slice thickness (mm) | 3.00 | 2.00 | 2.00 |
| In-plane resolution (mm) | 1.4 | 0.82 | 0.94 |
| Temporal resolution (s) | 68 | 58 | 55 |
| No. of contrast-enhanced images | 3 or 5[a] | 4 or 6 | 4 or 6[b] |
| Fat suppression | No | Yes | Yes |
| Parallel imaging | No | Yes | Yes |

FIG. 3

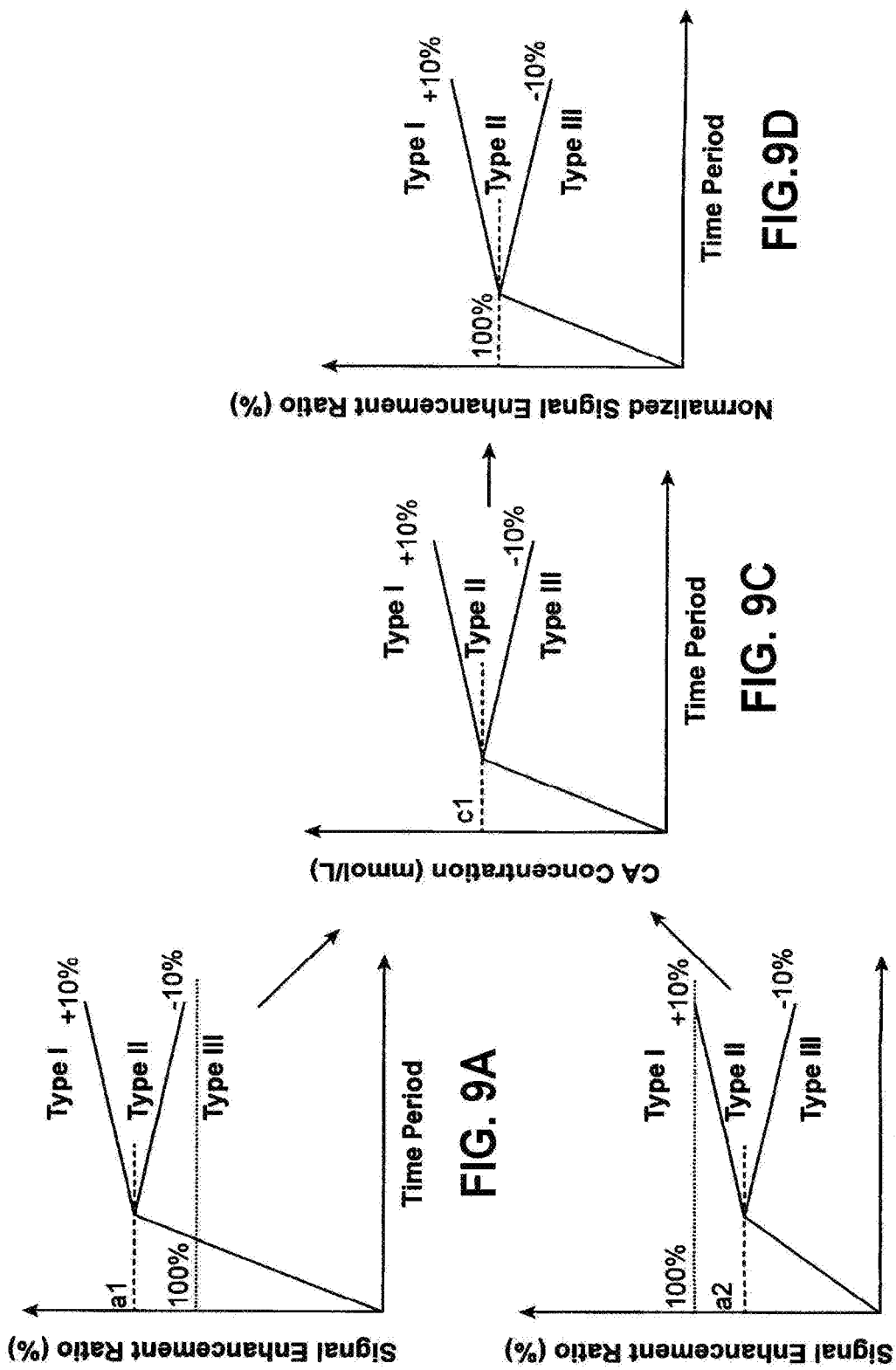

MRI DISPLAY OUTPUT REFLECTING CONTRAST AGENT CONCENTRATION AS A FUNCTION OF TIME

RELATED APPLICATION DATA

The present application is a continuation of U.S. patent application Ser. No. 14/384,636, filed Sep. 9, 2014, which is a National Phase Entry under 35 U.S.C. § 371 of International Patent Application No. PCT/US2013/032681, having an international filing date of Mar. 15, 2013, which claims the benefit under 35 U.S.C. § 119 to U.S. Provisional Application No. 61/611,877, filed Mar. 16, 2012, the contents of which are incorporated herein by reference as though set forth in full.

FIELD OF THE INVENTION

The subject matter of the disclosed invention relates to the acquisition and display of magnetic resonance imaging (MRI) information, and more particularly, to a system and method for analyzing MRI imaging information which computes and displays output information that reflects or is otherwise indicative of an absorption rate of a contrast agent in the volume of tissue.

CITED NON-PATENT PUBLICATIONS

The following non-patent publications are referenced in this specification:
1. Jansen, Shimauchi, Zak, Fan, Wood, Karczmar, Newstead. AJR 2009; 193:832-839, Kinetic Curves of Malignant Lesions are Not Consistent Across MRI Systems: Need for Improved Standardization of Breast Dynamic Contrast-Enhanced MRI Acquisition
2. C K Kuhl, P M Mielcareck, S Klaschnik, C Leutner, E Wardelmann, J Gieseke, H Schild, Radiology. 1999 211: 101-110. Dynamic Breast M R Imaging: Are Signal Intensity Time Course Data Useful for Differential Diagnosis of Enhancing Lesions?
3. Haacke E M, Tkach J A. Fast M R imaging: techniques and clinical applications. AJR Am J Roentgenol. 1990; 155(5):951-64.
4. Frahm J, Haase A, Matthaei D. Rapid three-dimensional MR imaging using the FLASH technique. J Comput Assist Tomogr. 1986; 10(2):363-8.
5. Tofts P S, Kermode A G. Measurement of the blood-brain barrier permeability and leakage space using dynamic M R imaging. 1. Fundamental concepts. MRM 1991; 17(2): 357-67.
6. Brix G, Semmler W, Port R, Schad L R, Layer G, Lorenz W J. Pharmacokinetic parameters in CNS Gd-DTPA enhanced M R imaging. J Comput Assist Tomogr. 1991; 15(4):621-8.
7. Rohrer M, Bauer H, Mintorovitch J, Requardt M, Weinmann H J. Comparison of Magnetic Properties of MRI Contrast Media Solutions at Different Magnetic Field Strengths. Invest Radiol. 2005; 40(11):715-24.
8. C Kuhl, Radiology. 2007 244:356-378. The Current Status of Breast MR Imaging.
9. Brix G, Kiessling F, Lucht R, Darai S, Wasser K, Delorme S, Griebel J. Microcirculation and Microvasculature in Breast Tumors: Pharmacokinetic Analysis of Dynamic MR Image Series. Magn Reson Med. 2004; 52(2):420-9.
10. Stanisz G J, Odrobina E E, Pun J, Escaravage M, Graham S J, Bronskill M J, Henkelimn R M. T1, T2 relaxation and magnetization transfer in tissue at 3T. Magn Reson Med. 2005; 54(3):507-12.

PATENT REFERENCES

Reference is further made to U.S. Pat. Nos. 7,693,320, 7,949,164 and 8,175,366, to Hadassa Degani et al., which disclose and describe methods and systems for reviewing and analyzing MRI imaging information related to the systems and methods disclosed and described herein, and the contents of which are hereby incorporated by reference as if fully set forth herein.

BACKGROUND

MRI imaging is well-known for medical applications, in which three dimensional (i.e., volumetric) imaging information of a patient's body region is acquired for diagnostic purposes. The MRI information may be acquired at a single point in time, or may be acquired at multiple points in time ("dynamic imaging"), in order to study the time progression of dynamic processes, such as the movement of blood.

There are a number of parameters that influence the strength of the signal obtained from an MRI scanner, and the appearance of the acquired image. Some of these parameters are controlled by the operator of the scanner, such as the repetition time TR, the echo time TE, and the flip angle $\alpha$. Other parameters are characteristics of the tissue being studied, such as the relaxation times T1 and T2. In principle, the unambiguous interpretation of an image involves only the observation and determination of the tissue dependent parameters, such as T1 and T2. In practice, however, these parameters are at least partially obscured by differing selections of TR and TE. Thus, it would be desirable to disentangle the effects of user-selected scanner parameters from the tissue-dependent imaging parameters.

Commercially available computer-controlled workstations employ a number of common types of displays to communicate useful information to a radiologist or technician (together hereinafter referred to "medical professional"). For example, MRI displays for the study of breast tissue, e.g., to identify the presence and location of cancer lesions, are well-known. Such MRI displays for breast tissue typically display images showing various two-dimensional slices taken through one or both breasts, and provide the medical professional with the ability to scroll through the respective tissue image slices using a common device, such as mouse. This scrolling enables the medical professional or other reviewer to readily view different slices, eventually covering the entire breast region.

Also, the medical professional or other reviewer may employ the MRI scanner to acquire volumetric image information of the breast/breasts using different MRI parameters to emphasize different physiological information. For example, "T2 weighted" images may be acquired with one set of acquisition parameters, and would show different information from "T1 weighted" images acquired with different scanner parameters. In addition, a set of images may be acquired before the administration of a contrast agent, and thereafter for several time periods after the contrast agent has entered the blood stream. The MRI workstation can be configured to display a selection of all of these image types, arranged in some order on a flat screen display. This arrangement of these multiple images is called the "hanging protocol," and is usually set up by the manufacturer according to the preferences of the particular reviewer.

In addition to the different acquired images described above, a flat panel display is typically provided for showing certain computed information, such as "maximum intensity projections" ("MIPs"), 3-D volume renderings, and a graph displaying signal intensity as a function of time, such as that shown in the screen capture displayed in FIG. 1. In particular, the "signal intensity" curves that appear in FIG. 1 depict the grey-level or pixel value at the user-selected voxel (y-axis) at each point in time (x-axis) in which the scanner acquired a time series of volumes. The first time point is taken before the introduction (e.g., by injection) of contrast agent into the patient's vasculature, and the subsequent time points after introduction of the contrast agent, typically spaced by approximately one minute per time point. Thus, each of the depicted signal intensity curves in FIG. 1 show a positive slope after the first time point, representing a "signal enhancement" taking place, which is due to the immediate increase in amount of contrast agent in the tissue volume being observed following introduction into the vasculature.

Of particular interest is the "shape" of the respective curve after the initial rapid enhancement. By "shape" is meant whether the slope of curve after the "knee" is positive, flat, or negative. The criterion generally accepted by the medical imaging community is that a slope less than +−10% is considered "flat" or "plateau", and beyond 10% either sustained enhancement or "washout." In particular, the shape of the curve is assumed to be indicative of different physiological conditions, and is often classified into three "Types," i.e., Type I, Type II or Type III, as shown in FIG. 2 (reproduced from Kuhl et al 2), with Type I associated with benign tissue (sub-types "Ia" and "Ib" are depicted in FIG. 2), Type II "suggestive of malignancy" (but often equivocal), and Type III associated with malignant lesions. With this in mind, in the screen capture shown in FIG. 1, curve 20 shows sustained enhancement; curve 22 shows Type I or rapid initial and sustained enhancement, curve 24 shows Type II or plateau behavior, and curve 26, indicating the most suspicious lesions, shows Type III or rapid initial enhancement with washout.

Notably, the manner in which the time progression of the signal intensity is displayed in FIG. 1 and FIG. 2 gives the reviewer the impression that the signal is, at least in some way, proportional to the amount of contrast agent in the tissue volume being studied. However, this is not necessarily the case. Furthermore, based on the way the signal intensity is displayed in these figures, the reviewer may mistakenly assume that the signal is linearly proportional to the amount of contrast agent. Again, this is not necessarily the case. Instead, as will be explained in detail herein, such linearity is actually a necessary condition for the assignment of a Type I to III to a volume of tissue to be independent of MRI scanner acquisition parameters, particularly TR, TE, and flip angle $\alpha$. Without such a linear relationship, a portion of tissue that appears as Type 1 or Type III, may change to Type II simply by being scanned with different acquisition parameters.

SUMMARY OF THE DISCLOSED INVENTIONS

In accordance with one aspect of the disclosed inventions, a magnetic resonant imaging (MRI) review workstation comprises a control processor, and a display integrated or otherwise operatively coupled with the control processor, wherein the control processor is configured to receive and analyze magnetic resonant imaging information pertaining to an imaged volume of tissue, and to cause to be displayed on the display output information that reflects or is otherwise indicative of an absorption rate of a contrast agent in the volume of tissue. In accordance with an object of the disclosed inventions, the output information provides an accurate indication of whether or not a wash out of the contrast agent occurred in the tissue volume during acquisition of the imaging information, regardless of a particular imaging system or imaging protocol employed to acquire the imaging information.

By way of example, the control processor may be configured to cause to be displayed a graphical representation of a concentration of the contrast agent in the tissue volume as a function of time during acquisition of the imaging information. By way of another example, the control processor may be configured to cause to be displayed a graphical representation of a signal intensity ratio in the tissue volume as a function of time, wherein the signal intensity ratio is normalized to take into account an actual absorption rate of the contrast agent in the tissue volume, wherein the control processor computes the normalized signal intensity ratio based, at least in part, upon a pre-contrast relaxation value of the tissue volume. In either case, the contrast agent concentration as a function of time may be computed by the control processor based, at least in part, upon a pre-contrast relaxation value of the tissue volume, and wherein the pre-contrast relaxation value of the tissue volume may be obtained using (i) a reference tissue method, (ii) direct measurement, or (iii a predetermined approximation. In one embodiment in which a reference tissue method is employed, the volume of tissue is breast tissue, and the reference tissue is pectoral muscle tissue or local fatty tissue. In various embodiments, the output information may comprise, or the control processor may be configured to additionally cause to be displayed, an absolute value of absorption of the contrast agent in the tissue volume.

In accordance with another aspect of the disclosed inventions, a system is provided to facilitate a review and analysis of magnetic resonant imaging information, wherein the system comprises at least one machine, the at least one machine respectively including a processor communicatively coupled to a storage device storing computer-executable instructions, which instructions, when executed by the processor, cause the processor to operate as: (i) a record module configured to acquire magnetic resonant imaging information pertaining to a volume of tissue; and (ii) a processing module configured to analyze magnetic resonant imaging information pertaining to a volume of tissue received by the record module, and to cause to be displayed on a display that is integrated or otherwise operatively coupled with the control processor output information that reflects or is otherwise indicative of an absorption rate of a contrast agent in the volume of tissue. Again, the output information preferably provides an indication of whether or not a wash out of the contrast agent occurred in the tissue volume during acquisition of the imaging information.

By way of one example, the processing module may be configured to cause to be displayed on the display a graphical representation of a concentration of the contrast agent in the tissue volume as a function of time during acquisition of the imaging information, wherein the contrast agent concentration as a function of time is computed based, at least in part, upon a pre-contrast relaxation value of the tissue volume. By way of another example, the processing module may be configured to cause to be displayed on the display a graphical representation of a signal intensity ratio in the tissue volume as a function of time, wherein the signal intensity ratio is normalized to take into account an actual absorption rate of the contrast agent in the tissue volume, regardless of a particular imaging system or imaging protocol employed to acquire the imaging information.

In accordance with still another aspect of the disclosed inventions, a method is provided for acquiring and evaluating magnetic resonance imaging (MRI) information, wherein the method includes the steps or acts of (i) acquiring MRI information of a volume of tissue over a period of time; (ii) using a processor to analyze the acquired MRI information; and (iii) displaying, on a display integrated or otherwise operatively coupled with the processor, information that reflects or is otherwise indicative of an absorption rate of a contrast agent in the volume of tissue during the period of time. In accordance with an object of the disclosed inventions, the output information preferably provides an indication of whether or not a wash out of the contrast agent occurred in the tissue volume during acquisition of the imaging information.

In one embodiment, the method includes the step or act of displaying on the display a graphical representation of a concentration of the contrast agent in the tissue volume as a function of time during acquisition of the imaging information, wherein the contrast agent concentration is computed as a function of time based, at least in part, upon a pre-contrast relaxation value of the tissue volume. In another embodiment, the method includes the step or act of displaying on the display a graphical representation of a signal intensity ratio in the tissue volume as a function of time, wherein the signal intensity ratio is normalized to take into account an actual absorption rate of the contrast agent in the tissue volume, regardless of a particular imaging system or imaging protocol employed to acquire the imaging information. In either case, the contrast agent concentration as a function of time may be computed by the control processor based, at least in part, upon a pre-contrast relaxation value of the tissue volume, and wherein the pre-contrast relaxation value of the tissue volume may be obtained using (i) a reference tissue method, (ii) direct measurement, or (iii) a predetermined approximation. In one embodiment in which a reference tissue method is employed, the volume of tissue is breast tissue, and the reference tissue is pectoral muscle tissue or local fatty tissue.

In various embodiments, the method may further comprise the step or act of introducing by injection or other means a contrast agent into the tissue volume.

These and other aspects and embodiments of the disclosed inventions are described in more detail below, in conjunction with the accompanying figures.

BRIEF DESCRIPTION OF THE DRAWINGS

FIG. 3 is a table showing the MRI systems and imaging protocols used in the Jansen et al. study.

FIG. 9A-D are respective graphical depictions of example signal enhancement ratio curves being "normalized" based on actual contrast agent absorption.

DETAILED DESCRIPTION OF THE DISCLOSED INVENTIONS

In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

In contrast to the prior art display modalities, a new display provided in accordance with one aspect of the disclosed inventions plots a concentration of contrast agent as a function of time, making the indirect connection between signal and concentration irrelevant. As explained herein, the concentration may be computed from the known physics of the MRI acquisition and the known acquisition parameters. Embodiments of the display are to be used with (as part of) an MRI display workstation, in which the time plot of contrast agent concentration may supplement or replace the presently used signal intensity plot depicted in FIG. 1, in order to more provide more accurate information to the medical professional for evaluating patient MRI information.

Figure 4C:
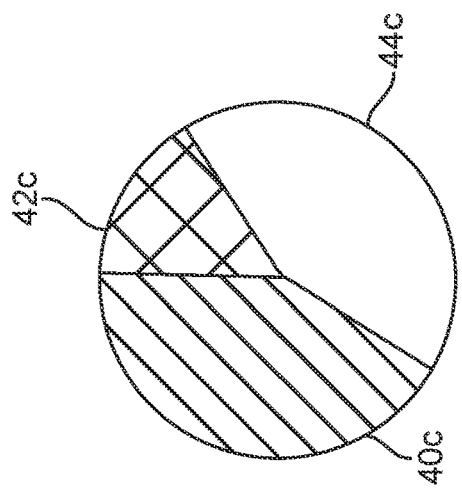
FIGS. 4A-4C are respective pie charts illustrating a proportion of cases in data sets exhibiting Types I, II and III curves for the respective different imaging systems used in the Jansen et al. study.
Figure 4B:
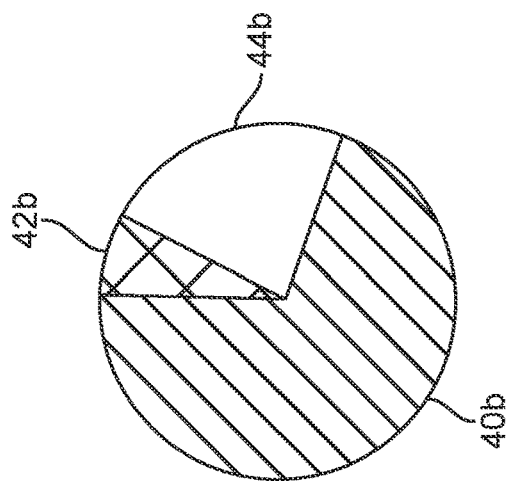
Figure 4A:
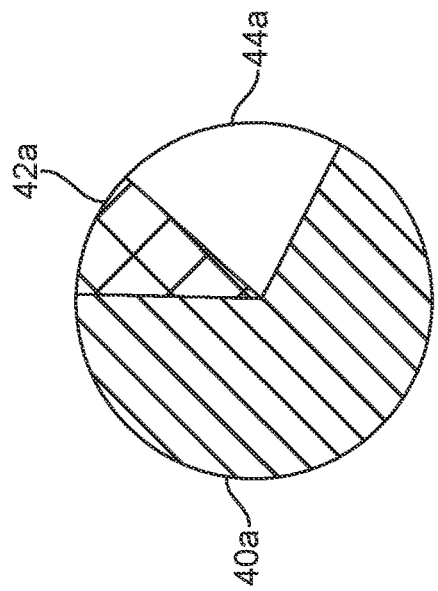

The difficulties resulting from the non-linear relationship between the signal and the concentration of contrast agent are demonstrated in Jansen et al [1], which describes a study performed of 601 patients, including 497 malignant and 185 benign lesions viewed on three different scanner/protocol combinations. The three data sets produced were called "System 1-3" by the authors, each group indicating which of the three scanner/protocol combinations was used for each individual case. The table shown in FIG. 3 summarizes the MRI systems and Protocols used in the study. The present inventors believe the parameters most responsible for differences are shown in the TR/TE row and the Flip angle. The finding of this study was that only 47% of Invasive ductal carcinoma (IDC) lesions imaged with System 3 exhibited washout type curves, compared with 75% and 74% of those imaged with System 1 and System, 2. These differences are shown graphically in the pie charts of FIGS. 4A-4C, in which:

FIG. 4A depicts the respective proportion of data sets exhibiting Type III washout (40a), Type II plateau (44a), and Type I persistent (42a) for System 1;

FIG. 4B depicts the respective proportion of data sets exhibiting Type III washout (40b), Type II plateau (44b), and Type I persistent (42b) for System 2; and FIG. 4C depicts the respective proportion of data sets exhibiting Type III washout (40c), Type II plateau (44c), and Type I persistent (42c) for System 3.

It is believed that many if not most medical professional base their diagnosis of the malignancy of a lesion largely on which of these curve types is characteristic of its time curve, with Type III being most indicative of cancer, Type I indicative of benign tissue, and Type II either suggestive or ambiguous. There is an intuitive explanation of why a malignant lesion would be expected to have a Type III curve having to do with the vascularity of lesions and vessel permeability. Breast cancer has increased vascularity with an increased permeability leading to an early uptake and early washout behavior, i.e., Type III. However, the results of the Jansen et al study, as summarized in the pie charts in FIGS. 4A-C, suggest that cases may be placed into different types or classifications, due of differences in scanner/protocol parameters used in the signal acquisition, not only because of underlying likelihood of malignancy. This would appear to be a very serious disadvantage of the present method of analyzing kinetic behavior.

Figure 1:
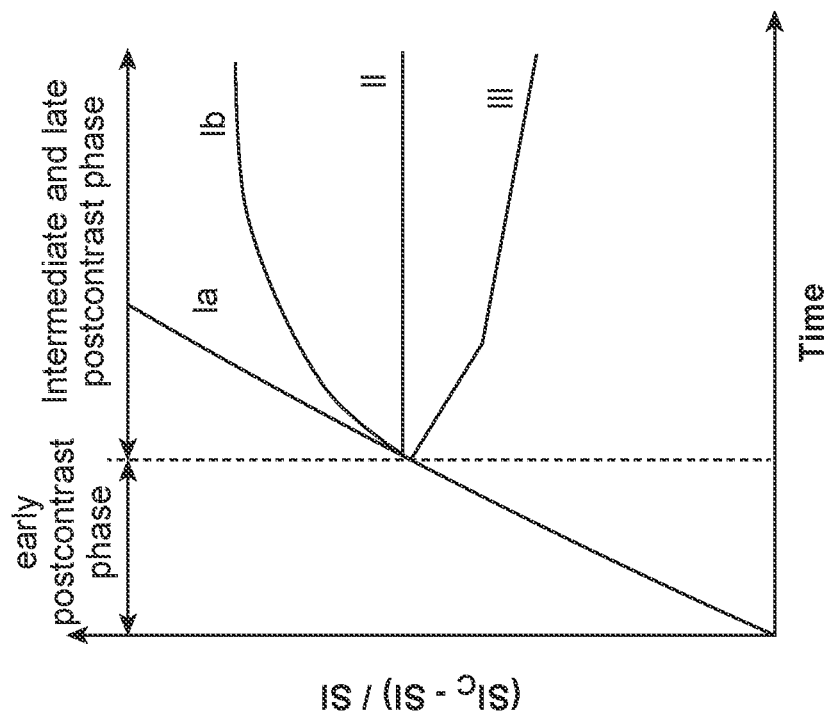
FIG. 1 is a captured MRI workstation display screenshot of a graph depicting relative signal intensity as a function of time.
Figure 2:
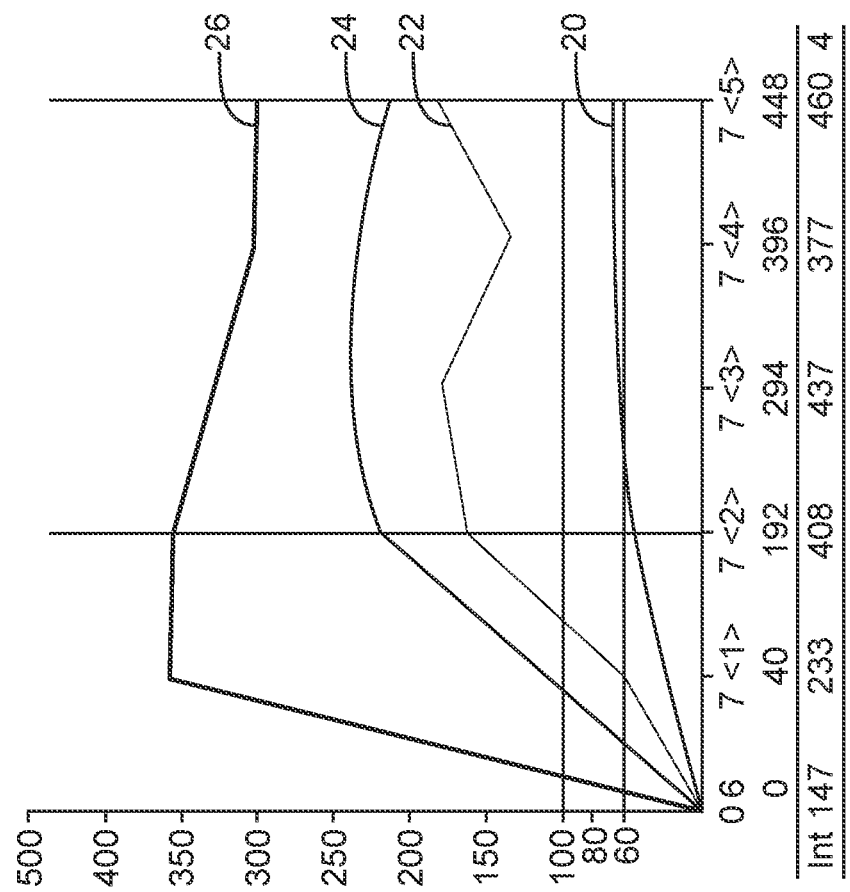
FIG. 2 is a graph reproduced from Kuhl et al 2, depicting exemplary signal intensity curves types I, II and III.

The present inventors believe this problem occurs as a result of the non-linear relationship between the MRI signal and the contrast agent concentration, in particular, in a signal of the type shown in FIG. 1, and not the concentration being observed and classified into Types I-III. In the spoiled gradient echo sequence, the standard method used in dynamic breast MRI, the signal intensity can be expressed as a function of tissue and acquisition parameters by equation 1 [3,4]:

$$S(t) = PD \times \sin\alpha \times \frac{1 - \exp(-TR/T_1)}{1 - \cos\alpha \exp(-TR/T_1)} \quad (1)$$

where P is the proton density, D is the scanner gain, a is the flip angle, and T1 is the tissue relaxation time, a characteristic of the tissue being examined.

The tissue relaxation time $T_1$ is related to the pre-contrast relaxation time $T_{10}$ and the local tissue relaxation rate $R_1$. This is assumed to be in a linear fashion as shown in equation 2 [5,6]:

$$\frac{1}{T_1} = \frac{1}{T_{10}} + R_{1CA}C(t) \quad (2)$$

where $R_{1CA}$ is treated as a known constant, uniquely determined by the choice of contrast agent [Rohrer et al 7].

Introducing equation 2 into equation 1, the relative signal enhancement is given by equation 3:

$$E(t) = \frac{S(t) - S(0)}{S(0)} = \frac{(1 - \exp\{-TR\{1/T_{10} + R_1 C_t(t)\}\})}{(1 - \exp\{-TR[1/T_{10} + R_1 C_t(t_0)]\}\cos\alpha)} \cdot \frac{[1 - \exp(-TR/T_{10})\cos\alpha]}{[1 - \exp(-TR/T_{10})]} - 1 \quad (3)$$

Relative signal enhancement allows the proton density to cancel out. This is the fundamental relationship between signal intensity E(t) and contrast agent concentration C(t), and it depends on many parameters that change between protocols, such as TR and flip angle α, and on parameters that depend on the tissue $T_{10}$. Specifically, this demonstrates a highly non-linear relationship between S(t) and C(t), meaning that the shape of the C(t) curve will not in general be preserved when transformed to S(t).

Figure 5B:
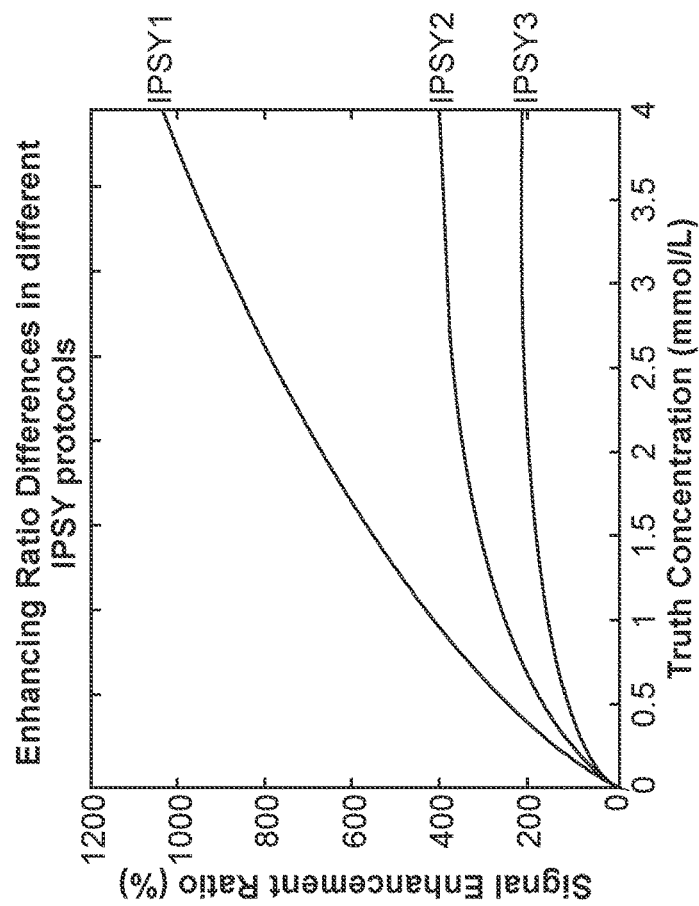
FIG. 5B depicts the signal enhancement ratio versus contrast agent concentration, respectively, from the 3 systems in Newstead et al with $T_{10}$ selected at 1200 ms.
Figure 5A:
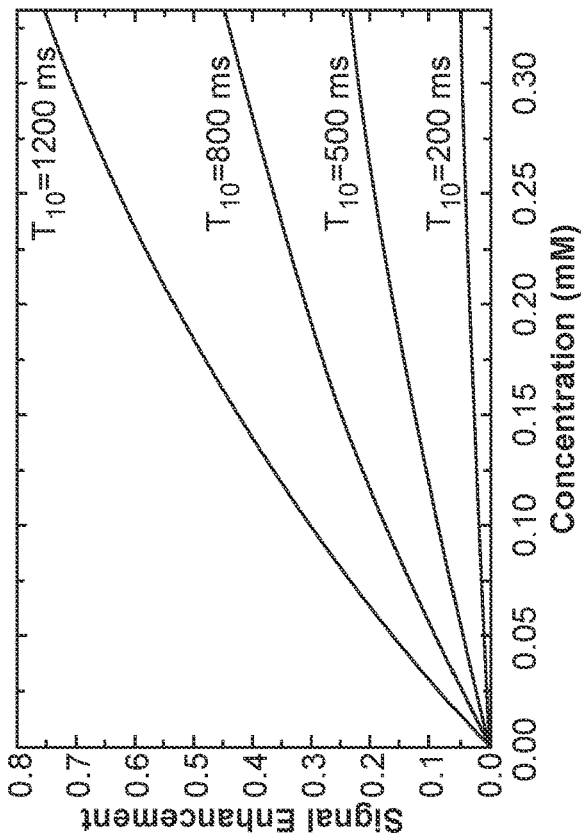
FIG. 5A depicts signal enhancement as a function of concentration for different values of $T_{10}$.

By way of demonstrative example, FIG. 5A depicts signal enhancement as a function of concentration for different values of $T_{10}$, and FIG. 5B depicts the signal enhancement ratio versus contrast agent concentration from the 3 systems in Newstead et al with $T_{10}$ selected at 1200 ms. One skilled in the art will be able to observe the non-linearity of the curves in FIG. 5A. In particular, the curve for System 3 even shows saturation at approximately 200%, i.e., the concentration can increase greatly without a significant increase in signal.

Figure 6:
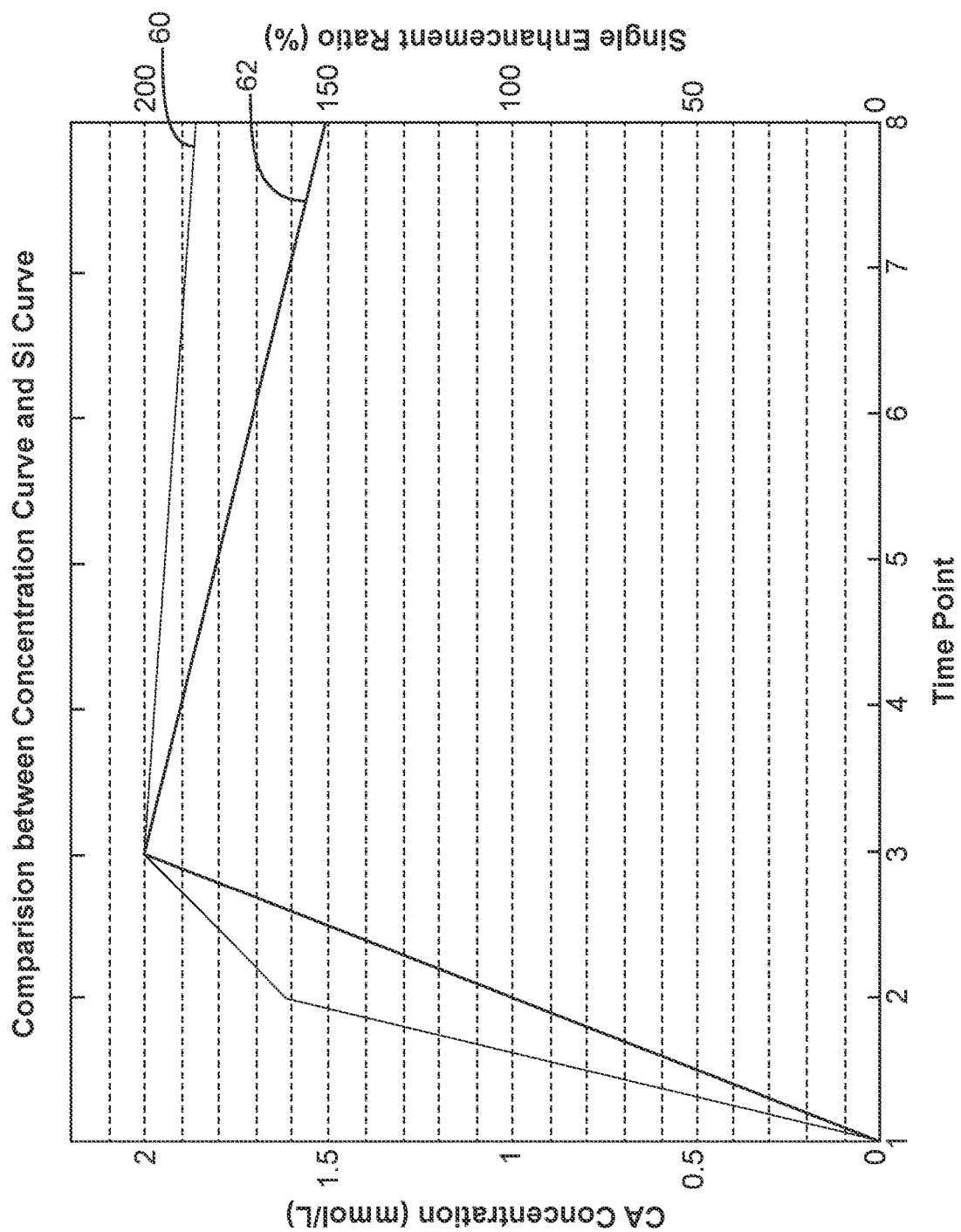
FIG. 6 is a graph depicting a first, hypothetical concentration curve exhibiting high initial uptake followed by rapid washout or type II, and a second, signal enhancement curve derived therefrom exhibiting high initial uptake followed by a plateau or Type II.

A hypothetical case demonstrates how a concentration curve with the suspicious time dependence of Type III can be turned into the ambivalent signal curve of Type II by this non-linear transformation. Curve 62 in FIG. 6 shows the hypothetical concentration curve exhibiting high initial uptake followed by rapid washout. The y-axis for concentration is shown at left and is in units of mmol/liter. Curve 60 shows the signal enhancement derived from this with the transformation shown in FIG. 6. The y-axis is on the right is in units of %. The peak concentration point occurring near time point 3 is depressed relative to later points due to the saturation of the concentration-signal curve. This tends to make a "peaking" distribution (Type III), flatter, or more like Type II. Clearly, in this case, shown in FIG. 6, the signal enhancement exhibits plateau behavior in spite of a clear Type III behavior of the concentration.

Similarly, a continuously increasing concentration of the Type I curve type can artificially plateau because of the saturation of the Signal/Concentration curve, and become a Type II signal curve. In retrospect it is believed that the intuitive expectation of the curve types is actually an expectation of the curve shape for concentration enhancement, which is generally assumed to be equivalent to the curve shape for signal enhancement, but this would only be true if the transformation from the former to the later were linear, which it is not.

Figure 7:
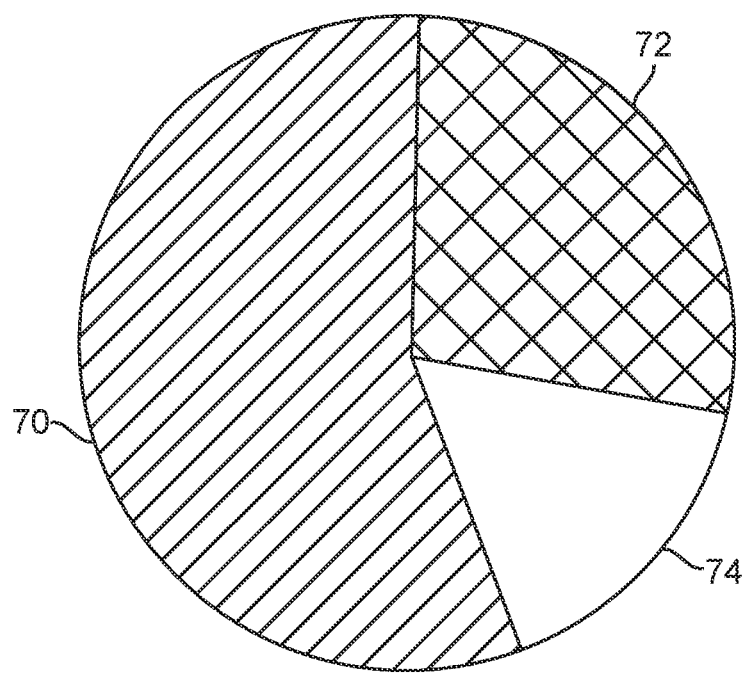
FIG. 7 is a pie chart in which the data depicted in FIG. 4C is corrected to accurately represent the distribution of curve types which is differentiated by washout ratio from peak enhancement.

Notably, the present inventors used the average peak signal enhancement ratio of malignant cancers in the UC data, and converted the ratio into contrast agent concentration to simulate the change in the pie chart shown in FIG. 4C. This is depicted in FIG. 7, which shows much closer agreement to System 1 and System 2, consistent with the proposition by the present inventors that the non-linear transformation from concentration to signal is responsible for the different proportions shown in FIG. 4C. Thus, one advantage of proving a display of kinetic information in the form of Contrast as a function of time, rather than signal versus time, is that contrast is the quantity that is directly related to the physiology of the lesion, independent of scanner parameters such as TR and TE and flip angle α, and thus avoids the adverse effects caused by non-linearity.

Having described and explained the advantage of displaying C(t) versus time over the traditional S(t) display, we now discuss in detail how the concentration can be obtained from the known physics of the MRI acquisition process and the known acquisition parameters.

The physics of the acquisition, given in Equation 4, repeated here:

$$E(t) = \frac{S(t) - S(0)}{S(0)} = \frac{(1 - \exp\{-TR\{1/T_{10} + R_1 C_t(t)\}\})}{(1 - \exp\{-TR[1/T_{10} + R_1 C_t(t_0)]\}\cos\alpha)} \frac{[1 - \exp(-TR/T_{10})\cos\alpha]}{[1 - \exp(-TR/T_{10})]} - 1 \quad (4)$$

This well-known equation, sometimes called the "FLASH" equation, is correct for the spoiled gradient echo sequence, which is the most commonly used sequence for breast MRI [8]. Other sequences, such as "TURBO_FLASH", although rarely used in breast MRI applications, will have other known equations relating Signal E(t) to Concentration C(t). In this equation, the repetition time TR and flip angle α are parameters set by the operator of the scanner. $R_1$ is the rate constant, measured in other experiments to be 4.3 to 6.7 L/mml s, depending on the type of Gadolineum Chelate used [7]. The remaining parameter in this equation is $T_{10}$, the pre-contrast value of tissue $T_1$. Although "textbook" values for $T_{10}$ may be taken from published measurements of "typical tissue," these numbers can have significant errors when applied to different individuals, and do not adequately take into account the variability observed in an actual tissue lesion.

Alternative methods of measuring the $T_{10}$ value at each voxel of the imaged volume from the individual patient include T1 mapping, which requires at least one, and preferably two extra volume acquisitions prior to injection of CA, each acquisition using a different flip angle α. This method can be understood by considering the signal equations for the commonly used scanner sequences used in breast imaging (SPGR, FFE, or FLASH). In these sequences a series of low flip angle RF pulses are used within a short TR period. The signal from an FFE sequence with flip angle α across the whole slice is given by equation 5:

$$\rho(a) = \rho_0 \frac{1 - e^{-TR/T_1}}{1 - \cos a \times e^{-TR/T_1}} \sin a \quad (5)$$

A computationally simple method for estimating T1 can be obtained by manipulating equation 4 and rearranging into the form shown below in equation 6.

$$\frac{\rho(a)}{\sin a} = e^{-TR/T_1} \frac{\rho(a)}{\tan a} + \rho_0(1 - e^{-TR/T_1}) \quad (6)$$

Note that a plot of ρ/(sin α vs ρ/tan α) at different values of flip angle forms a straight line with slope a=exp(-TR/T1). T1 can therefore be obtained as:

$$T1 = -TR/\ln(a) \quad (7)$$

To obtain the slope then requires at least two sequences with different flip angles, or, for better accuracy, three flip sequences with different flip angles. T1 mapping therefore requires extra volume acquisitions, each one adding approximately a minute to the total patient procedure. It may happen that this extra scanning time is prohibitively expensive for many medical facilities, and for this reason the present inventors prefer a further alternative approach using reference tissue instead of textbook values or T1 mapping. In particular assuming, as in conventional DCE-MRI protocols, the use of short TR and small flip angle, the relative signal $S(0)/S_{ref}(0)$ (as opposed to the absolute signal S(0) of a lesion) is relatively insensitive to the actual protocol adjustment of MRI system. In this case the following linear relation can be used to estimate the pre-contrast relaxation $T_{10}$.

$$\frac{S(0)}{S_{ref}(0)} = \frac{[1 - \exp(-TR/T_{10ref})\cos\alpha](1 - \exp(-TR/T_{10}))}{[1 - \exp(-TR/T_{10})\cos\alpha](1 - \exp(-TR/T_{10ref}))} \approx \frac{T_{10ref}}{T_{10}} \quad (8)$$

where $S_{ref}(0)$ is the signal intensity of muscle tissue prior to contrast agent injection and $T_{10ref}$ is a $T_1$ relaxation time of muscle tissue before contrast agent injection. S(0) and $T_{10}$ are the signal and $T_{10}$ value respectively of the tissue of interest.

Figure 8B:
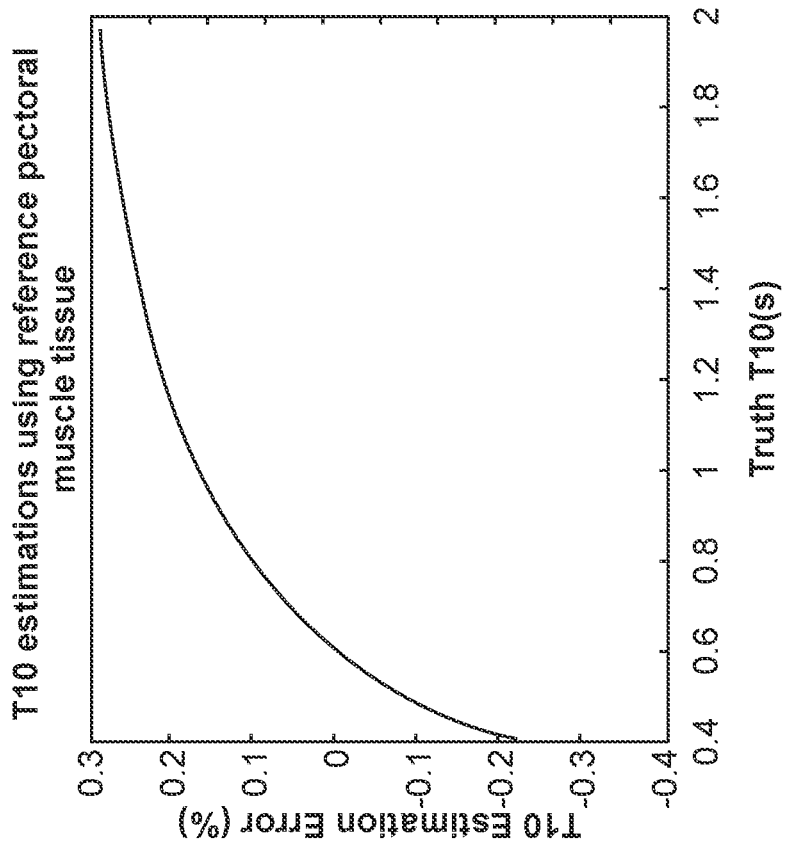
FIGS. 8A and 8B are graphs depicting $T_{10}$ estimation using the Reference Tissue method.
Figure 8A:
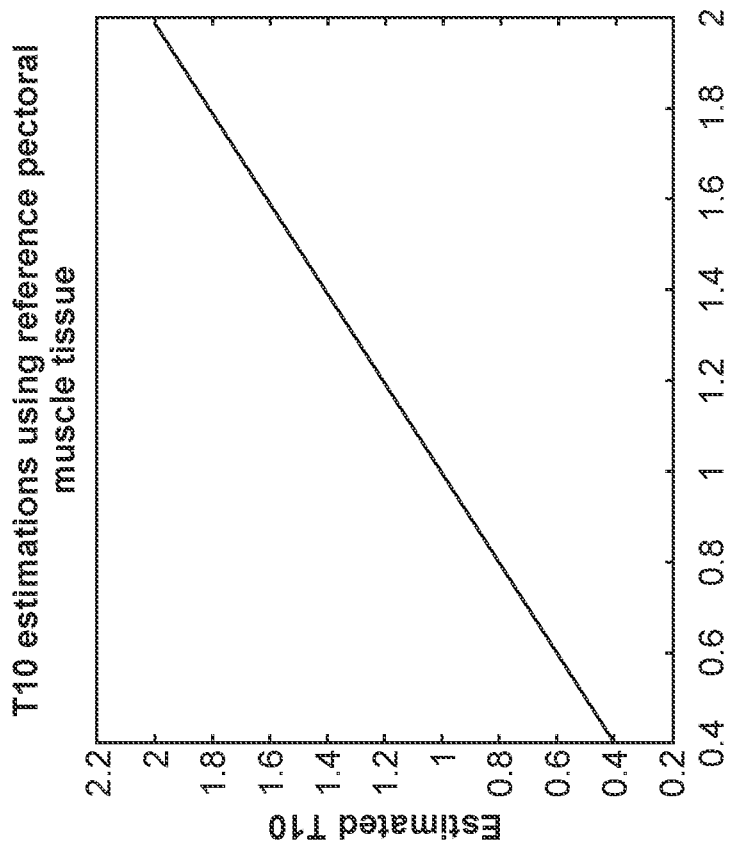

As depicted in FIGS. 8A and 8B, by assuming the measured value for breast pectoral muscle of the $T_1$ relaxation time of 607 ms [9], the $T_{10}$ estimated from equation 4 using a standard DCE-MRI protocol (TR/TE:5.2/2.5 ms, FA:10 as recommended by the QIBA panel) results in less than 0.3% error in a range from 400 ms to 2000 ms of true $T_{10}$ values. The graph of FIG. 8B shows the maximum error occurring at very large values of T1, but with most of the T1 range with a much smaller error. Brix's [9] study also confirms the viability of using the relative signal ratio $(S(0)/S_{fat}(0))$ to estimate the lesion T1 relaxation value.

Two uncertainties in this method might include B1 inhomogeneity and what literature value of $T_{10}$ of normal pectoral muscle [9] tissue is used. The present inventors believe the former is not a concern and that the Reference Tissue method is robust to B1 inhomogeneity error because of the low flip angle used in the DCE-MRI protocol for breast. For example, using the same imaging protocol as in FIG. 8, but with a large B1 inhomogeneity that results in a 50% change in the signal still yields less than 3% of error in the $T_{10}$ estimation. Thus, while obtaining the pre-contrast value $T_{10}$ using the above-described "Reference Tissue" method can result in a possible error due an erroneous literature value of $T_{10}$, such error (especially if pectoral muscle is chosen as the reference tissue), should not substantially impact on the accuracy of the estimated and displayed contrast agent in the patient tissue volume as a function of time.

Proposed MRI Review Workstation

In view of the foregoing, the present invention provides an improved MRI review workstation display, in which output information is displayed in conjunction with the patient imaging data that reflects or is otherwise indicative of an absorption rate of a contrast agent in the volume of tissue. While the form and content of the output information may vary depending on the particular system display design and reviewer preferences, what is important is that the displayed output information provides an accurate indication of whether or not a "wash out" of the contrast agent occurred in the tissue volume during acquisition of the imaging information, regardless of a particular imaging system or imaging protocol employed to acquire the imaging information.

By way of non-limiting example, the output information may be a graphical representation of a concentration of the contrast agent in the tissue volume as a function of time during acquisition of the imaging information. Alternatively and/or additionally, the output information may be a graphical representation of a signal intensity ratio in the tissue volume as a function of time, wherein the signal intensity ratio is normalized to take into account an actual absorption rate of the contrast agent in the tissue volume. These options are shown in FIGS. 9A-D, which demonstrates how the imaging data reflected in what appear to be disparate signal enhancement ratio curves shown in FIGS. 9A and 9B obtained for the same tissue volume using different MRI systems into and/or imaging protocols can instead be reflected (i.e., converted) into the absorption rate curve shown in FIG. 9C, which in turn can be converted back to a signal enhancement ratio curve shown in FIG. 9D that has been "normalized" so that the displayed curve accurately reflects the tissue volume image data notwithstanding the differences in the imaging system and/or protocol used to acquire the imaging data.

Thus, as is depicted in FIGS. 9A-D, the MRI review workstation controller (aka "control processor") of embodiments of the present invention is preferably programmed to compute the so-called normalized signal intensity ratio based, at least in part, upon a pre-contrast relaxation value of the tissue volume. Also, regardless of the particular form of the displayed output information, the contrast agent concentration as a function of time is preferably computed by the workstation control processor based, at least in part, upon a pre-contrast relaxation value of the tissue volume. As explained above, the pre-contrast relaxation value of the tissue volume may be obtained using any of (i) a Reference Tissue method, (ii) direct measurement, or (iii a predetermined approximation. In an embodiment in which the tissue volume being imaged is breast tissue, a Reference Tissue method is preferably employed, wherein the reference tissue is pectoral muscle tissue or local fatty tissue. It may also be desired to have the output information comprise), or otherwise include, an absolute value of absorption of the contrast agent in the tissue volume.

Figure 10:
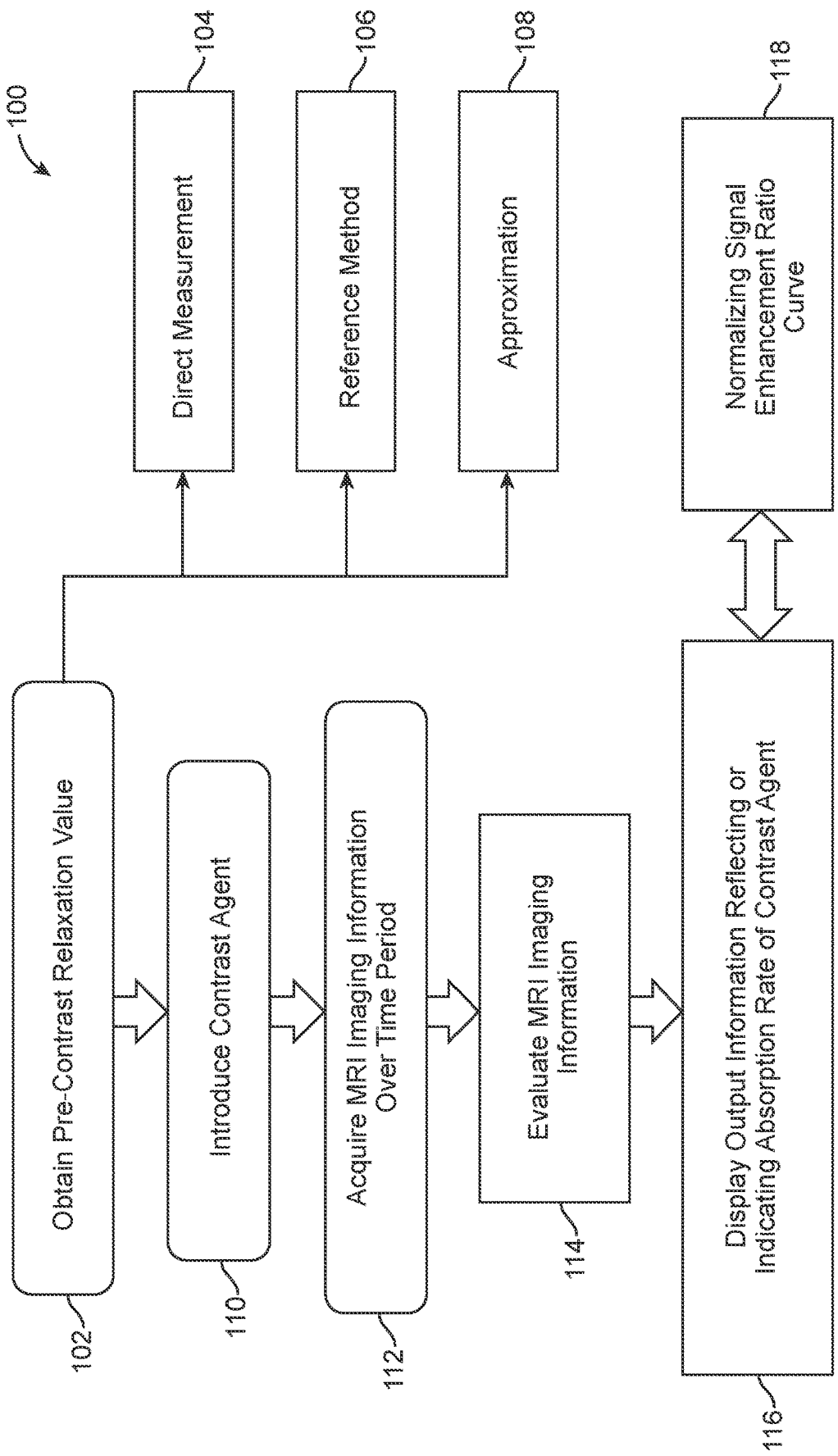
FIG. 10 is a flow diagram depicting an MRI imaging acquisition and analysis method carried out according to one embodiment of the invention.

With reference to FIG. 10, in accordance with still another aspect of the disclosed inventions, a method is provided for acquiring and evaluating magnetic resonant imaging (MRI) information of a volume of tissue, such as but not limited to breast tissue. The method 100 includes, at step 102, obtaining a pre-contrast relaxation value for the tissue volume. This can be accomplished by any one of alternative steps 104, using a reference tissue method, 106, directly measuring the relaxation value prior to introducing the contrast agent, or 108, using a predetermined approximation for the respective tissue volume.

Thereafter, at step 110, the contrast agent is introduced into the subject's vasculature, e.g., by injection or other means. Then, at step 112, MRI imaging information of the tissue volume is acquired over the requisite time period. At step 114, the imaging information is analyzed/evaluated, i.e., by the review workstation processor, and at step 116, the workstation displays on a display integrated or otherwise operatively coupled with the workstation, output information that reflects or is otherwise indicative of an absorption rate of a contrast agent in the volume of tissue during the period of time, wherein the output information provides an indication of whether or not a wash out of the contrast agent occurred in the tissue volume during acquisition of the imaging information. As discussed above, the contrast agent concentration is computed as a function of time based, at least in part, upon a pre-contrast relaxation value of the tissue volume. As also discussed above, the output information may include displaying a graphical representation of a signal intensity ratio in the tissue volume as a function of time, wherein, as indicated at step 118 in FIG. 10, the signal intensity ratio is normalized to take into account an actual absorption rate of the contrast agent in the tissue volume.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. Thus the above specific embodiments are illustrative, and many variations can be introduced on these embodiments without departing from the scope of the appended claims.

The invention claimed is:

1. A computer-implemented method for processing magnetic resonant imaging (MRI) data, the computer-implemented method comprising:

receiving, at a MRI workstation, respective electronic MRI data of an imaged volume of tissue acquired by different MRI scanners over respective periods of time after respective contrast agents were introduced into a patient while at least a portion of the patient was positioned within respective different MRI scanners;

executing, by a control processor of the MRI workstation, instructions stored in a computer readable medium to analyze the respective electronic MRI data pertaining to the imaged tissue volume and determine a converted result reflecting or indicating an absorption rate of the respective contrast agent in the imaged tissue volume and that compensates for a non-linear relationship between an MRI signal generated by an MRI scanner during imaging of the tissue volume and the contrast agent concentration over time, the control processor deriving the converted result based on a signal intensity ratio for the imaged tissue volume that has been normalized to take into account an actual absorption rate of the respective contrast agent in the imaged tissue volume, wherein the signal intensity ratio is normalized by the control processor executing a plurality of conversions comprising:

a first conversion of a plurality of disparate signal enhancement ratio curves associated with the different MRI scanners into an absorption rate curve, and a second conversion of the absorption rate curve into a signal enhancement ratio curve normalized to reflect or indicate the tissue volume image data notwithstanding the different MRI scanners that were used to acquire the respective electronic MRI data; and presenting, by a display of the MRI workstation operably coupled to the control processor and to a user of the MRI workstation, the converted result reflecting or indicating the absorption rate of the respective contrast agent in the imaged tissue.

2. The computer-implemented method of claim 1, the electronic MRI data comprising first electronic MRI data acquired by a first MRI scanner, second electronic MRI data acquired by a second MRI scanner different from the first MRI scanner, and third electronic MRI data acquired by a third MRI scanner different from the first MRI scanner and the second MRI scanner, wherein the MRI workstation receives the respective first, second and third electronic MRI data from the respective first, second and third MRI scanners.

3. The computer-implemented method of claim 1, wherein the converted result is presented to the user of the MRI workstation during acquisition of electronic MRI data by an MRI scanner.

4. The computer-implemented method of claim 1, wherein the converted result is based at least in part upon a pre-contrast relaxation value of the tissue volume as determined by the different MRI scanners.

5. The computer-implemented method of claim 4, wherein the pre-contrast relaxation value of the tissue volume is a value obtained using a reference tissue method, wherein the reference tissue is pectoral muscle tissue or local fatty tissue, and the tissue volume is breast tissue.

6. The computer-implemented method of claim 4, wherein the pre-contrast relaxation value of the tissue volume is a value obtained by direct measurement prior to introduction of the respective contrast agent into the tissue volume.

7. The computer-implemented method of claim 4, wherein the pre-contrast relaxation value of the tissue volume is based on a predetermined approximation.

8. The computer-implemented method of claim 1, further comprising presenting, by the display of the MRI workstation and to the user, an absolute value of absorption of the respective contrast agent in the tissue volume.

9. The computer-implemented method of claim 1, wherein the respective contrast agent is introduced into the patient by injection of the respective contrast agent into the patient's vasculature.

10. The computer-implemented method of claim 9, further comprising introducing the respective contrast agent into the patient's vasculature, wherein the respective electronic MRI data is acquired by the respective MRI scanner while the respective contrast agent travels through the patient's vasculature.

11. The computer-implemented method of claim 1, wherein the converted result compensates for the non-linear relationship between the MRI signal and the contrast agent concentration over time caused by at least one operating parameter of the MRI scanner that generates the MRI signal.

12. The computer-implemented method of claim 11, wherein the at least one operating parameter is at least one of repetition time (TR), echo time (TE), and flip angle $\alpha$.

13. The computer-implemented method of claim 1, wherein the converted result provides an accurate indication of whether or not a wash out of the respective contrast agent has occurred in the imaged tissue volume during acquisition of the respective electronic MRI data by the different MRI scanners.

14. The computer-implemented method of claim 1, wherein the respective electronic MRI data of the imaged volume of tissue acquired by the different MRI scanners correspond to the disparate signal enhancement ratio curves comprising a first signal enhancement ratio curve and a second signal enhancement ratio curve obtained for the same imaged tissue volume by the different MRI scanners, wherein the respective first and second signal enhancement curves are associated with respective Type I-III curves for the imaged tissue volume, a Type I curve indicating benign tissue, a Type II curve being suggestive of potential cancer and a Type III curve being most indicative of cancer compared to the Type I curve and the Type II curve.

15. The computer-implemented method of claim 14, the converted result comprising the signal enhancement ratio curve that is normalized to take into account the actual absorption rate of the respective contrast agent in the imaged tissue volume and that portrays whether or not a wash out of the respective contrast agent occurred in the imaged tissue volume during acquisition of the respective electronic MRI data.

16. The computer-implemented method of claim 1, further comprising generating the respective electronic MRI data by activation of at least one MRI scanner.

17. A computer-implemented method for processing magnetic resonant imaging (MRI) data, the computer-implemented method comprising:

receiving, at a MRI workstation, respective electronic MRI data of an imaged volume of tissue acquired by different MRI protocols by at least one MRI scanner over respective periods of time after respective contrast agents were introduced into a patient while at least a portion of the patient was positioned within the at least one MRI scanner;

executing, by a control processor of the MRI workstation, instructions stored in a computer readable medium to analyze the respective electronic MRI data pertaining to the imaged tissue volume and determine a converted result reflecting or indicating an absorption rate of the respective contrast agent in the imaged tissue volume and that compensates for a non-linear relationship between an MRI signal generated by the at least one MRI scanner during imaging of the tissue volume and the contrast agent concentration over time, the control processor deriving the converted result based on a signal intensity ratio for the imaged tissue volume that has been normalized to take into account an actual absorption rate of the respective contrast agent in the imaged tissue volume, wherein the signal intensity ratio is normalized by the control processor executing a plurality of conversions comprising:

a first conversion of a plurality of disparate signal enhancement ratio curves associated with the different MRI protocols into an absorption rate curve, and a second conversion of the absorption rate curve into a signal enhancement ratio curve normalized to reflect or indicate the tissue volume image data notwithstanding the different MRI protocols that were used to acquire respective electronic MRI data; and presenting, by a display of the MRI workstation operably coupled to the control processor and to a user of the MRI workstation, the converted result reflecting or indicating the absorption rate of the respective contrast agent in the imaged tissue.

18. A computer-implemented method for processing magnetic resonant imaging (MRI) data, the computer-implemented method comprising:

receiving, at a MRI workstation, respective electronic MRI data of an imaged volume of tissue acquired by different MRI scanners executing respective different MRI protocols over respective periods of time after respective contrast agents were introduced into a patient while at least a portion of the patient was positioned within respective MRI scanners;

executing, by a control processor of the MRI workstation, instructions stored in a computer readable medium to analyze the respective electronic MRI data pertaining to the imaged tissue volume and determine a converted result reflecting or indicating an absorption rate of the respective contrast agent in the imaged tissue volume and that compensates for a non-linear relationship between an MRI signal generated by the at least one MRI scanner during imaging of the tissue volume and the contrast agent concentration over time, the control processor deriving the converted result based on a signal intensity ratio for the imaged tissue volume that has been normalized to take into account an actual absorption rate of the respective contrast agent in the imaged tissue volume, wherein the signal intensity ratio is normalized by the control processor executing a plurality of conversions comprising:
  a first conversion of a plurality of disparate signal enhancement ratio curves associated with the different MRI scanners executing different MRI protocols into an absorption rate curve, and
  a second conversion of the absorption rate curve into a signal enhancement ratio curve normalized to reflect or indicate the tissue volume image data notwithstanding the different MRI scanners executing respective different MRI protocols that were used to acquire the respective electronic MRI data; and
presenting, by a display of the MRI workstation operably coupled to the control processor and to a user of the MRI workstation, the converted result reflecting or indicating the absorption rate of the respective contrast agent in the imaged tissue.

* * * * *